United States Patent
Boussignac et al.

(10) Patent No.: US 6,273,087 B1
(45) Date of Patent: Aug. 14, 2001

(54) RESPIRATORY AID

(76) Inventors: Georges Boussignac, 1, Avenue de Provence, Antony, 92160; Jean-Claude Labrune, 19A Rue Massenet, Sevres, 92310, both of (FR)

( * ) Notice: Subject to any disclaimer, the term of this patent is extended or adjusted under 35 U.S.C. 154(b) by 0 days.

(21) Appl. No.: 09/319,307
(22) PCT Filed: Oct. 26, 1998
(86) PCT No.: PCT/FR98/02280
§ 371 Date: Jun. 3, 1999
§ 102(e) Date: Jun. 3, 1999
(87) PCT Pub. No.: WO99/21603
PCT Pub. Date: May 6, 1999

(30) Foreign Application Priority Data

Oct. 27, 1997 (FR) .................................................. 97 13430

(51) Int. Cl.$^7$ .................................................. A61M 16/00
(52) U.S. Cl. .................. 128/204.22; 128/204.23; 128/205.23; 128/202.22; 128/202.27; 128/200.12; 128/204.25; 128/912; 600/531; 600/532; 600/543
(58) Field of Search .................. 128/204.22, 204.23, 128/205.23, 202.22, 202.27, 200.12, 204.25, 912, 203.16, 203.15, 203.18; 604/58; 600/531, 532, 543

(56) References Cited

U.S. PATENT DOCUMENTS

| 3,661,528 | 5/1972 | Falk ..................................... 23/254 R |
| 3,881,480 | * 5/1975 | Lafourcade ........................ 128/145.8 |
| 4,207,884 | * 6/1980 | Isaacson ........................... 128/200.24 |
| 4,558,708 | * 12/1985 | Labuda et al. ........................ 128/719 |
| 4,592,349 | * 6/1986 | Bird .................................. 128/204.25 |
| 4,679,573 | * 7/1987 | Parnoff et al. ........................ 128/716 |
| 4,852,583 | * 8/1989 | Walker .................................. 128/716 |
| 5,036,847 | 8/1991 | Boussignac et al. . |
| 5,166,075 | * 11/1992 | Fehder .................................. 436/133 |
| 5,335,656 | * 8/1994 | Bowe et al. ...................... 128/207.18 |
| 5,452,715 | 9/1995 | Boussignac . |
| 5,465,728 | * 11/1995 | Phillips ................................. 128/730 |
| 5,474,060 | 12/1995 | Evans . |
| 5,538,002 | 7/1996 | Boussignac et al. . |
| 5,642,726 | * 7/1997 | Owens et al. .................... 128/200.26 |
| 5,789,660 | * 8/1998 | Kofoed et al. ......................... 73/23.2 |
| 5,893,361 | * 4/1999 | Hughes ........................... 128/200.24 |
| 5,979,444 | * 11/1999 | Sherrod ........................... 128/205.25 |
| 6,129,680 | * 10/2000 | Mottram ................................ 600/532 |

FOREIGN PATENT DOCUMENTS

| 0390684 | 3/1990 | (EP) . |
| 0640355 | 7/1994 | (EP) . |
| 0701834 | 9/1995 | (EP) . |
| 2267661 | 12/1993 | (GB) . |
| WO 97/06843 | 2/1997 | (WO) . |

* cited by examiner

Primary Examiner—John G. Weiss
Assistant Examiner—Mital Patel
(74) Attorney, Agent, or Firm—Fisher, Christen & Sabol

(57) ABSTRACT

A tubular respiratory assistance device which forms the wall of a main channel and is intended to be connected by its distal end to a patient's airway, so that the main channel connects the patient's respiratory system to the outside, and which has at least one auxiliary channel which is associated with deflection means for injecting a respiratory gas jet which is deflected toward the interior of the main channel and is intended to ventilate the patient. The tubular respiratory assistance device also has an annular chamber arranged at the periphery of it, coaxially with it on its distal end, and a distal annular orifice, the annular chamber communicating with the patient's respiratory system by means of the distal annular orifice and being provided with means for connection to the outside. Also, a respiratory assistance mask intended to be fitted to a patient's face which has this tubular respiratory assistance device for inlet and outlet of respiratory gas.

9 Claims, 3 Drawing Sheets

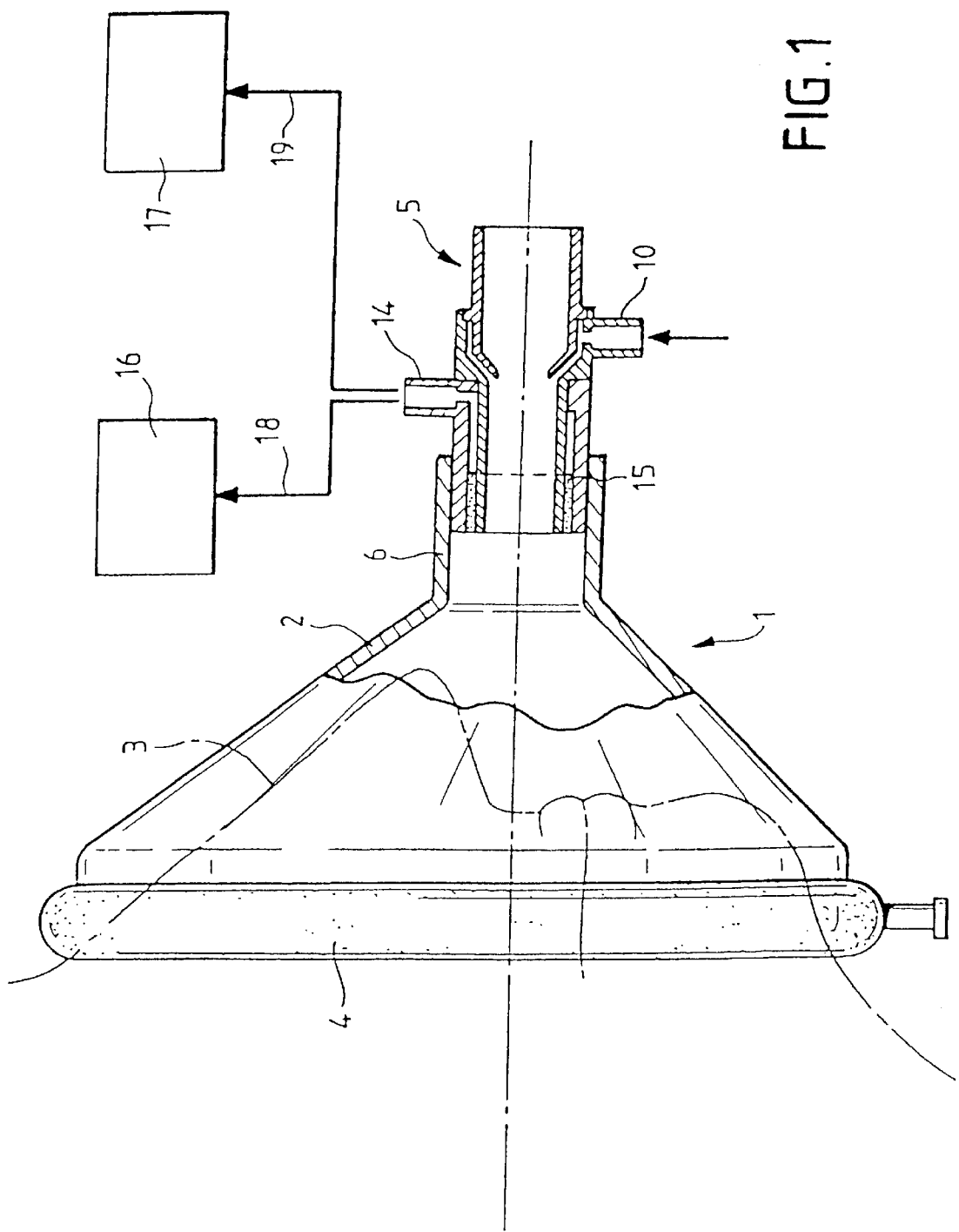

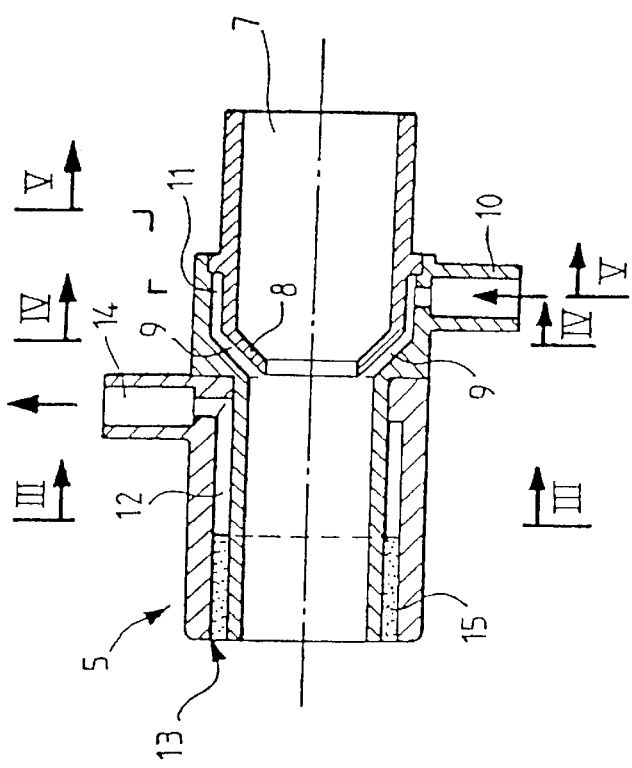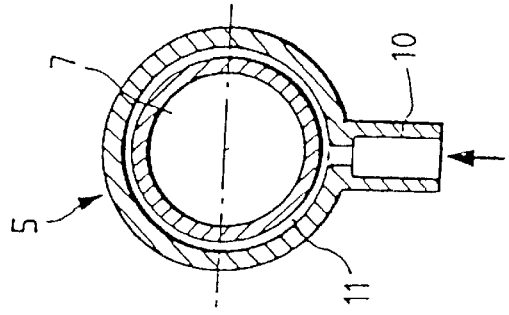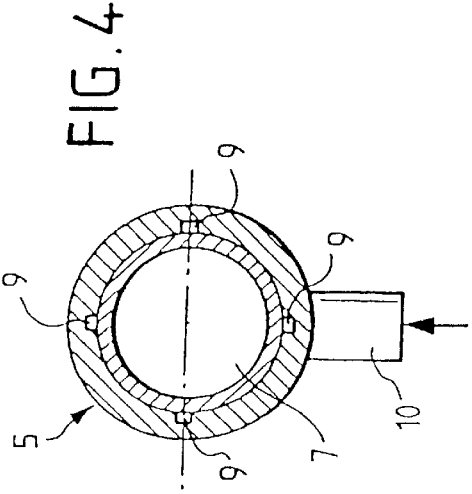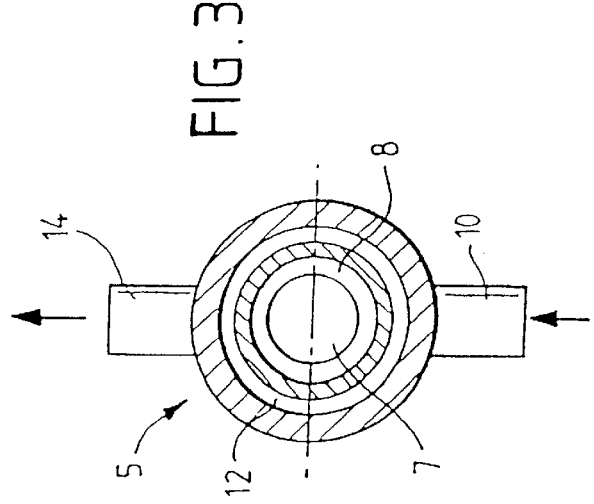

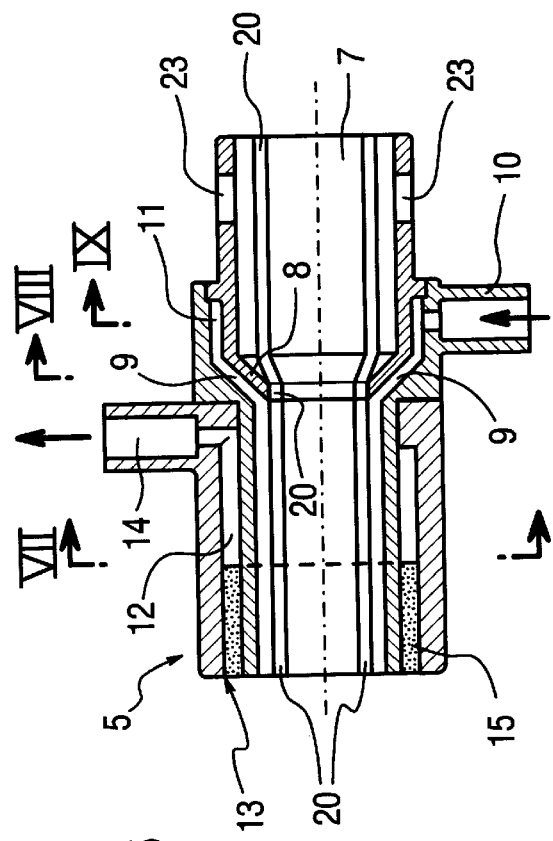
FIG. 6
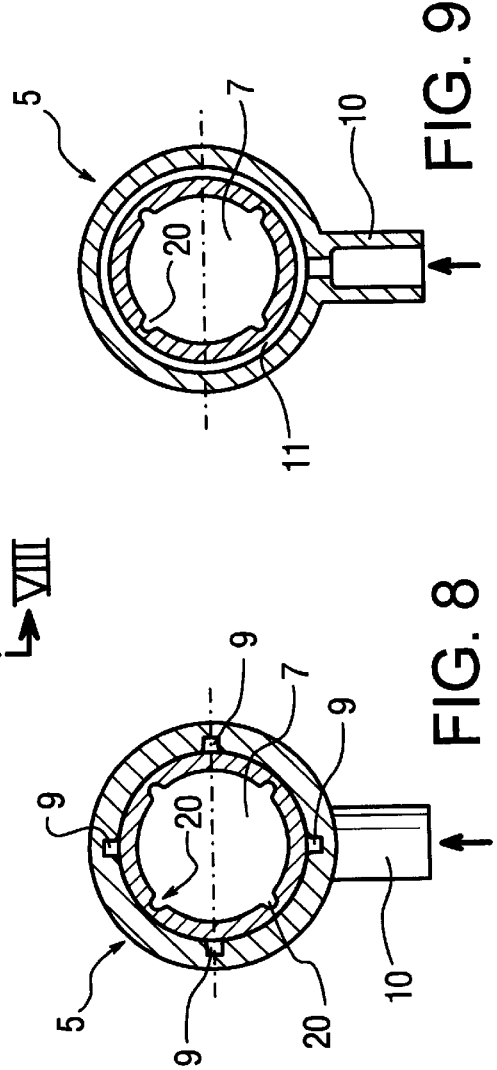
FIG. 8
FIG. 9
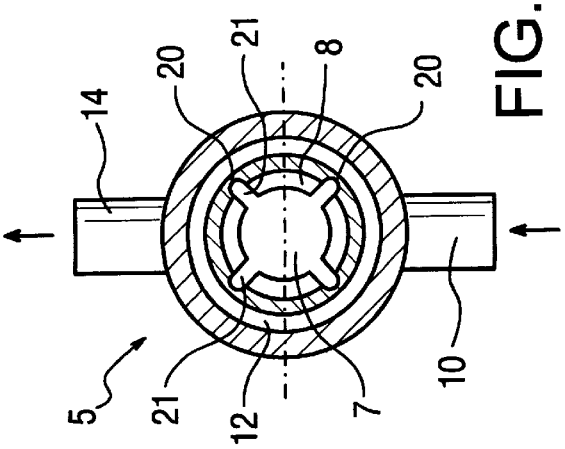
FIG. 7

RESPIRATORY AID

The present invention relates to a respiratory assistance device which can be used on patients whose spontaneous respiration is absent or insufficient, whether or not they are placed under artificial respiration.

European Patent EP-A-0 390 684 (U.S. Pat. No. 5,036, 847) has already disclosed a tubular respiratory assistance device, which forms a main channel and which is intended to be connected by its distal end to a patient's airway so that said main channel connects said patient's respiratory system to the outside, said device having at least one auxiliary channel associated with deflection means for injecting a respiratory gas jet which is deflected toward the interior of said main channel and is intended to ventilate said patient.

The object of the present invention is to improve such a device so that the doctor can ascertain the gas pressure and/or the gas composition in said patient's airway.

To that end, according to the invention, the respiratory assistance device of the type summarized above is noteworthy in that it has, on the distal side, an annular chamber arranged at the periphery of said tubular device, coaxially with it and communicating with the patient's respiratory system by means of the orifice formed by its distal annular section, and in that said annular chamber is provided with means for connection to the outside.

It is thus possible to measure the pressure and/or determine the composition of the gas contained in said chamber. It will be noted that this gas is identical to the one prevailing in the respiratory system but is quietened compared with it because of its partial isolation by the chamber. The measurements are therefore reliable, avoiding the consequences of gas turbulence.

In particular for the purpose of rendering the gas contained in the chamber homogeneous, it is then preferable for said means of connection to the outside to be arranged at the proximal end of said chamber.

In the case where the gases contained in said chamber need to undergo compositional analysis and pressure measurement, said chamber should have a relatively large volume, corresponding to the quantity of gas needed for the analysis. Turbulence capable of inducing strong variations in the pressure measurements may then occur in said chamber.

In order to avoid this, it is advantageous to provide means for damping gas turbulence, such as a fibrous or porous filter, in said chamber.

As security in addition to an optional pressure measurement device, it is advantageous for the device according to the present invention to have a network of grooves made in the wall of the main channel and at least one orifice passing through the proximal part of said device so as to form an access to the atmosphere for said patient's respiratory system, in the event of accidental obstruction of the proximal part of said device.

There are many possible applications for the tubular respiratory assistance device according to the invention. It may be used as a buccal or nasal probe, or alternatively as an adapter attached to a tracheotomy tube. It may also, in a respiratory mask intended to be fitted to a patient's face, constitute the tubular adapter for inlet and outlet of the respiratory gas. In this case, said chamber is in communication with the patient's respiratory system via the interior of said mask.

When it is used as a respiratory mask adapter, the respiratory assistance device according to the present invention may be integral with said mask. However, in particular in order for it to be usable on its own, without a mask, it may be advantageous for said device to be fitted removably to said mask, for example by engagement.

The figures of the appended drawing will clearly show how the invention may be embodied. In these figures, identical references denote similar elements.

FIG. 1 is a schematic view, partially in axial section, of a respiratory assistance mask having a tubular device according to the present invention.

FIG. 2 shows, in axial section, said tubular device constituting the adapter of the mask in FIG. 1.

FIGS. 3, 4 and 5 are cross sections of the device in FIG. respectively on the lines III—III, IV—IV and V—V.

FIG. 6 shows, in axial section similar to FIG. 2, an alternative embodiment of the tubular device according to the present invention.

FIGS. 7, 8 and 9 are cross sections of the device in FIG. 6, respectively on the lines VII—VII, VIII—VIII and IX—IX.

The respiratory assistance mask 1, according to the present invention and represented in FIG. 1, has a rigid shell of frustoconical general shape 2, which can be fitted to a patient's face 3 by means of an inflatable cushion 4 bordering its peripheral opening. On the opposite side, said mask 1 has a tubular device 5, fixed or engaged on a tubular projection 6 of said shell 2. The tubular device 5 is used as an adapter for inlet and outlet of respiratory gas into and from the mask 1. It may optionally be connected to artificial respiration equipment by its proximal end (on the opposite side from the patient 3).

As shown in more detail by FIGS. 2 to 5, the tubular device 5 has an internal through-passage 7 and, in the central part, a conical wall 8 protruding inside aid passage 7. The conical wall 8 has the purpose of deflecting, in the direction of the axis of the passage 7, respiratory gas jets injected through peripheral channels 9, supplied from a feed adapter 10, by means of a peripheral annular chamber 11.

Further, on the distal side, the tubular device 5 has an annular peripheral chamber 12, coaxial with said device 5. The annular peripheral chamber 12 communicates with the interior of the mask 1 by its distal annular orifice 13 and is provided, at its proximal end, with an outlet adapter 14.

A fibrous or porous (cotton wool, synthetic foam, etc.) filter 15 is arranged in the annular peripheral chamber 12, in order to damp the gas turbulence and therefore excessive pressure variations.

As represented in FIG. 1, the outlet adapter 14 may be connected to a gas analyzer 16 or to a pressure measuring device 17. Of course, the connections 18 and 19 between the outlet adapter 14 and the devices 16 and 17 are intended so that the sampling of gas to be analyzed through the connection 18 has no effect on the pressure measurement via the connection 19.

Thus, by virtue of the devices 16 and 17, the doctor attending the patient 3 constantly knows the composition of the gas in the mask 1 (and in particular its carbon dioxide level) and the pressure inside said mask. He can therefore take the appropriate intervention measures according to said composition and pressure of the gas.

In the alternative embodiment of the device 5, which is shown by FIGS. 6 to 9, the elements 7 to 15 described above with reference to FIGS. 2 to 5 are again found. However, it may be noted that this alternative embodiment also has, in the wall of the passage 7 and in the conical wall 8, grooves 20, arranged radially between the peripheral channels 9, as well as at least one orifice 23 passing through the wall of the proximal end of the device 5. Thus, if for any reason the proximal part of the device 5 is obstructed, the grooves 20, and the orifices 23 constitute an access to the atmosphere, preventing the pressure of the respiratory gas injected from reaching excessive values which may be dangerous for the patient. This provides automatic operational security, supplementing the optional pressure measuring device 17.

Although they have not been respected [sic] in the figures, it is clear that the device 5 may have channels or ducts for injecting medication and/or water.

Further, although a particular application of the device 5 to a respiratory mask was described above with the aid of said figures, it will be readily understood that said device has many other possible applications, for example as a nasal probe, buccal probe, tracheal probe, etc. Of course, the dimensions of said device will be adapted to each particular use.

What is claim is:

1. A tubular respiratory assistance device having a distal end and a proximal end, said tubular device forming the wall of a main channel and being intended to be connected by said distal end to a patient's airway so that said main channel connects the respiratory system of said patient to the outside, said tubular device having at least one auxiliary channel associated with deflection means for injecting a respiratory gas jet which is deflected toward the interior of said main channel and is intended to ventilate said patient, wherein said tubular device has, on said distal end, an annular chamber arranged at a periphery of and coaxial with the main channel of said tubular device and having a distal annular orifice, said annular chamber being capable of communicating with the respiratory system of said patient by means of said distal annular orifice and of containing gases exhaled by said patient being provided with means for connection to compositional analysis and pressure measurement means for said exhaled gases, and wherein a means for damping gas turbulence is arranged in said annular chamber.

2. The respiratory assistance device according to claim 1, wherein said annular chamber has a proximal end opposite said distal annular orifice and wherein said connecting means is arranged at the proximal end of said annular chamber.

3. The respiratory assistance device according to claims 1, wherein said means for damping gas turbulence is formed by a filter of a porous material.

4. The respiratory assistance device according to claim 1, wherein said means for damping gas turbulence is formed by an annular filter of a fibrous material.

5. The respiratory assistance device according to claim 1, wherein, said main channel having a wall formed by said tubular device, said device comprises a network of grooves made in said wall of said main channel and at least one orifice passing through said proximal end of said tubular device so as to form an access to the atmosphere for said patient's respiratory system, in the event of an accidental obstruction of said proximal end of said tubular device.

6. A respiratory assistance mask intended to be fitted to the face of a patient having an adapter for inlet and outlet of respiratory gas, wherein said adapter is a tubular device having a distal end and a proximal end, said tubular device forming a main channel and being connected by said distal end to said mask so that said main channel connects the respiratory system of said patient to the outside, said tubular device having at least one auxiliary channel associated with deflection means for injecting a respiratory gas jet which is deflected toward the interior of said main channel and is intended to ventilate said patient, said tubular device having, on said distal end, an annular chamber arranged at a periphery of and coaxial with the main channel of said tubular device and having a distal annular orifice, said annular chamber being capable of communicating with the respiratory system of the patient by means of said distal annular orifice and of containing gases exhaled by said patient being provided with means for connection to compositional analysis and pressure measurement means for said exhaled gases, and wherein a means for damping gas turbulence is arranged in said annular chamber.

7. The respiratory assistance mask according to claim 6, wherein said tubular device is integral with said mask.

8. The respiratory assistance mask according to claim 6, wherein said tubular device is fitted removably to said mask.

9. The respiratory assistance mask according to claim 8, wherein said tubular device can be engaged on said mask.

* * * * *